US007989851B2

(12) United States Patent
Lu et al.

(10) Patent No.: US 7,989,851 B2
(45) Date of Patent: Aug. 2, 2011

(54) MULTIFUNCTIONAL BIOSENSOR BASED ON ZNO NANOSTRUCTURES

(75) Inventors: Yicheng Lu, East Brunswick, NJ (US); Ying Chen, Piscataway, NJ (US); Zheng Zhang, Belle Mead, NJ (US)

(73) Assignee: Rutgers, the State University of New Jersey, New Brunswick, NJ (US)

( * ) Notice: Subject to any disclaimer, the term of this patent is extended or adjusted under 35 U.S.C. 154(b) by 1233 days.

(21) Appl. No.: 11/600,556

(22) Filed: Nov. 16, 2006

(65) Prior Publication Data
US 2007/0210349 A1 Sep. 13, 2007

Related U.S. Application Data

(63) Continuation-in-part of application No. 11/119,475, filed on Apr. 29, 2005, now abandoned, which is a continuation of application No. 10/456,050, filed on Jun. 6, 2003, now Pat. No. 6,914,279.

(60) Provisional application No. 60/385,884, filed on Jun. 6, 2002, provisional application No. 60/736,852, filed on Nov. 16, 2005.

(51) Int. Cl.
*H01L 29/82* (2006.01)
*H03H 9/56* (2006.01)

(52) U.S. Cl. ........... 257/252; 257/79; 257/253; 257/414; 257/E23.165; 257/E29.081; 257/E29.093; 257/E33.005; 257/E51.04; 310/313 A; 310/313 B; 310/313 R; 333/133; 333/187

(58) Field of Classification Search ............... 257/79, 257/252, 253, 414, E23.165, E29.081, E29.093, 257/E33.005, E51.04; 310/313 A, 313 B, 310/313 R; 333/133, 187
See application file for complete search history.

(56) References Cited

U.S. PATENT DOCUMENTS

| 6,304,020 | B1 * | 10/2001 | Lonsdale et al. | ........... 310/313 B |
| 6,914,279 | B2 * | 7/2005 | Lu et al. | .......................... 506/39 |
| 2002/0093398 | A1 * | 7/2002 | Ella et al. | ....................... 333/187 |
| 2007/0132043 | A1 * | 6/2007 | Bradley et al. | ................. 257/414 |

* cited by examiner

*Primary Examiner* — Dao H Nguyen
(74) *Attorney, Agent, or Firm* — Hoffman & Baron, LLP

(57) ABSTRACT

The present invention provides the multifunctional biological and biochemical sensor technology based on the integration of ZnO nanotips with bulk acoustic wave (BAW) devices, particularly, quartz crystal microbalance (QCM) and thin film bulk acoustic wave resonator (TFBAR). ZnO nanotips provide giant effective surface area and strong bonding sites. Furthermore, the controllable wettability of ZnO nanostructured surface dramatically reduces the liquid consumption and enhances the sensitivity of the biosensor device.

8 Claims, 12 Drawing Sheets (a)

(b)

(c)

(a)

(b)

(a)

(b)

(a)

(b)

(c)

(a)

(b)

(a)

(b)

MULTIFUNCTIONAL BIOSENSOR BASED ON ZNO NANOSTRUCTURES

CROSS-REFERENCE TO RELATED APPLICATION

This application claims the benefit of U.S. Provisional Patent Application No. 60/736,852 filed on Nov. 16, 2005 and is a Continuation in Part of application Ser. No. 11/119,475 filed on Apr. 29, 2005 now abandoned which is a continuation of application Ser. No. 10/456,050 filed on Jun. 6, 2003, now U.S. Pat. No. 6,914,279, and which claims the benefit of U.S. Provisional Patent Application No. 60/385,884, which was filed on Jun. 6, 2002, the contents of all of which are incorporated herein by reference.

This invention was made with Government support under Grant Nos. NSF ECS-0088549 and NSF CCR-0103096, awarded by the National Science Foundation. Therefore, the Government has certain rights in this invention.

FIELD OF THE INVENTION

This invention relates generally to biosensor technology, and pertains more particularly to novel multifunctional biosensors based on zinc oxide (ZnO) nanostructures for biological, biochemical, chemical and environmental applications. More particularly, this invention addresses the new sensor technology based on integration of ZnO nanostructures with quartz crystal microbalance (QCM) and with thin film bulk acoustic wave resonator (TFBAR). Metalorganic chemical vapor deposition (MOCVD) growth technology is used to obtain transparent and highly conductive, semiconductive, or piezoelectric ZnO nanotips and their arrays on surfaces of QCM and TFBAR devices. These ZnO nanotips can be used as biological/chemical molecule binding sites or reacted with interesting elements in gas. ZnO nanotip arrays deposited on QCM will dramatically increase the effective sensing area. Such nanostructured QCM sensor can be used for chemical and biochemical detection in liquid phase or gas phase. On the other case, ZnO nanotips deposited on TFBAR structures can be used for gas and liquid phase sensing. It also can be integrated with microfluidics for sensing system. The advantages of such novel nanostructured TFBAR devices include: (i) high frequency operation therefore leads to the high sensitivity, (ii) can be integrated with Si IC as it can be built on the Si substrates, (iii) can be wireless as the device operates in the frequency domain. (iv) it is compatible with thin film microelectronics processing technology, therefore, is cost-effective and can be mass-production.

Furthermore, the ZnO nanotips covered sensing surfaces possess controllable wettability. It can be in superhydrophobic or superhydrophilic status. The superhydrophilic sensing surfaces reduce the liquid consumption and further enhance the sensitivity.

These integrated devices possess both the advantages of piezoelectric devices (QCM and TFBAR) and ZnO nanostructures. Such integrated devices also have many advantages, such as high manufacturability and low cost. It leads to the new sensor technology, which has broad applications.

BACKGROUND OF THE INVENTION

The nanoscale science and engineering have shown great promise for the fabrication of novel nano-biosensors with faster response and higher sensitivity than that of planar sensor configurations, due to their small dimensions combined with dramatically increased contact surface and strong binding with biological and chemical reagents which could have important applications in biological and biochemical research, as well as in environmental monitoring and protection.

ZnO nanostructures have many advantages. As disclosed in U.S. patent application Ser. No. 10/243,269, nanotip arrays made with semiconductive, insulating or conductive ZnO can be fabricated in a controlled manner to produce tips with a uniform size, distribution and orientation. The ZnO nanotips are made using our chemical vapor deposition (CVD)-based method in a simple process at relatively low temperatures as disclosed by S. Muthukumar*, H. Sheng*, J. Zhong*, Z. Zhang*, N. W. Emanaetoglu*, Y. Lu, "Selective MOCVD Growth of ZnO Nanotips", *IEEE Trans. Nanotech*, Vol. 2, n. 1, pp. 50-54 (2003), giving ZnO nanostructures a unique advantage over other wide bandgap semiconductor nanostructures, such as gallium nitride (GaN) and silicon carbide (SiC). Furthermore, through proper doping and alloying, ZnO nanotips can be made as semiconductor with different doping level, piezoelectric, transparent and conducting, and magnetic, thus having multifunctional sensing applications.

Recent advances in genetic sequencing methods are leading to an explosion in the area of biotechnology. Many emerging areas of biotechnology are based upon highly-parallel methods for sequencing and detecting DNA, RNA, and proteins. Many of these areas could benefit greatly by leveraging the emerging nanotechnology, but applying it to develop and utilize new analytical tools for biochemical analysis. A need exists to provide novel biological and biochemical sensors, which have higher sensing efficiency and multiple functionality, thereby having significant advantages in comparison to the existing sensor technology.

ZnO is emerging as a major wide band gap semiconductor material. It also possesses unique multifunctional properties, which are critically important for new sensor technology. ZnO nanostructures have become one of the most important and useful multifunctional nanostructures. It can be grown at low temperature on various substrates. ZnO nanostructures have been found broad applications in optoelectronics, electronics, catalysts, and especially, for high sensitivity sensor technology.

TFBAR is one of the key devices for RF IC, signal processing, frequency control, and sensors, which offers advantages, such as small size, high frequency operation, low insertion loss, and lower power consumption. They are also attractive for the capability of monolithic integration with Si ICs, leading to miniaturization and reducing cost. The integration of ZnO nanotips with TFBAR technology will lead to the new nanosensors, particularly wireless sensor devices inheriting advantages from both technologies. It can operate at the high frequency range (in GHz range).

On the other hand, QCM has been widely used as the sensor devices for various gas detection, immunosensor, DNA biosensor, and drug analysis in many areas of biological, food, environmental and clinical analysis. It has many advantages, such as high-quality (Q) factor, typically 10,000 to 100,000 at room temperature, which leads to the high sensitivity, low-cost and commercially availability. The integration of ZnO nanotips with QCM leads to another new nanosensors inheriting advantages from both technology. It operates at the relatively low frequency range (1-100 MHz range).

Such novel sensors can be used to detect various gas and biological molecules interactions of DNA-DNA, DNA-RNA, protein-protein, and protein-small molecules, for examples, glucose and uric acid detection. Some of new commercial applications include:

(i) New methods for the prevention, diagnosis and treatment of diseases;

(ii) Detection of gas phase and liquid phase chemical and biochemical agents, and hazardous chemicals for homeland defense against bioterrorism activities following the 9/11 attacks;

(iii) Environmental monitoring and protection due to its multifunctional material properties (semiconductor, piezoelectric, transparent and conductive, etc.). The nano-patterned and uniformly distributed ZnO nanotip arrays on TFBAR and QCM sensors can efficiently and accurately detect the presence of targets in a given sample due to affinity between molecules and nanotips.

Some of the advantages presented by the sensors according to the present invention include the following:

(i) ZnO as metal oxide semiconductor is an excellent sensing material. It has been used to sense various gaseous species, such as $NO_x$, CO, $H_2$, $NH_3$, etc. When it is integrated to QCM and TFBAR, it dramatically extends these two popular BAW sensor technologies, and enhances the performances.

(ii) ZnO can be grown as thin films or as nanoscale structures. Nanoscale sensors show great promise, as they have faster response and higher sensitivity than planar sensor configurations, due to their smaller dimensions combined with dramatically increased sensing surface and strong binding properties. We have demonstrated that ZnO nanotips can greatly enhance DNA and protein immobilization.

(iii) Wettability control of ZnO nanostructured sensor surfaces can greatly reduce the liquid consumption and further enhance the sensitivity.

(iv) ZnO is a multifunctional material, which is excellent for sensor technology. It is a wide bandgap semiconductor. With proper doping, ZnO can be made as semiconductive, transparent and conductive, piezoelectric, or ferromagnetic. It has excellent optical, electrical and acoustic properties. The integration of some or all of these functions into one single sensor platform, or by arraying the different types of ZnO nanosensors into a chip will enhance the sensitivity and accuracy.

(v) It can be used for both gas and liquid phase sensing. It also can be integrated with microfluidics, especially useful for future sensor-on-chip and lab-on-chip technologies.

(vi) It can be used for the low-power and wireless sensor devices.

(vii) ZnO nanotips and tip-arrays can be grown and patterned at the surface of semiconductors, (such as Si, GaN, etc.), glass, $SiO_2$ film, metals and single crystal substrates (e.g. $LiNbO_3$, quartz, $Al_2O_3$, etc.) at low temperature (~400° C.). The direct integration of ZnO nanotips with popular QCM and TFBAR offers advantages of the novel sensor technology: excellent manufactability and the large-scale production.

In contrast to conventional sensor technologies, the invented sensor integrates QCM and TFBAR with ZnO nanostructures. Therefore, this type of new sensors possess advantages of both technologies of QCM and TFBAR, (such as ease and low cost of fabrication, being rugged, and convenience of operation), and of nanoscale sensors (such as high efficiency, accuracy, and rapid response).

In addition, unique multifunctional sensing mechanisms enhance measurement reliability and accuracy operating in gaseous, as well as in liquid environments. It is feasible for integration to make system-on-a-chip or lab-on-a-chip technology. Compared to planar sensors, nanoscale sensors will respond significantly faster with substantially higher sensitivity.

Furthermore, due to the unique chemical properties high-density ZnO nanotip arrays will be used for the diagnostic kits and flow-through systems. This represents an opportunity for development of miniaturized cost-effective devices for clinical applications.

SUMMARY OF THE INVENTION

It is the primary objective of this invention to address the novel multifunctional biosensor technology based on ZnO nanotips and nanotip arrays.

Particularly, it is an objective of this invention to provide highly sensitive biological and chemical sensors by integrating ZnO nanotips with bulk acoustic wave (BAW)-based devices, particularly, the QCM and TFBAR. The wettability of such nanostructured sensor surfaces can be controlled. The superhydrophilic sensing surfaces reduce the liquid consumption and further enhance the sensitivity.

As ZnO nanotips can be made semiconducting, transparent and conducting, or piezoelectric, their unique electrical, optical and acoustic properties can serve as the basis for multifunctional sensors. A sensor chip comprising of arrays and combinations of various types of ZnO nanotip-based biosensors also allow for multimode and multipurpose operations.

BRIEF DESCRIPTION OF THE DRAWINGS

FIG. 1 (b) shows a schematic of top view of the conductivity-based ZnO nanotip biosensor structure.

FIG. 3 (b) shows a schematic of a top view of ZnO nanotip SAW sensor.

FIG. 4 (b) shows a plot of a phase shift as a function of frequency between the reference and test ZnO nanotip SAW sensor devices.

FIG. 9 (b) depicts a $S_{21}$ (transmission) spectra before and after DNA oligonucleotide immobilization from a ZnO nanotip-based SAW biosensors.

FIG. 10 (b) shows optical microscope pictures of the TFBAR device.

DETAILED DESCRIPTION OF THE TECHNOLOGY

Figure 1:
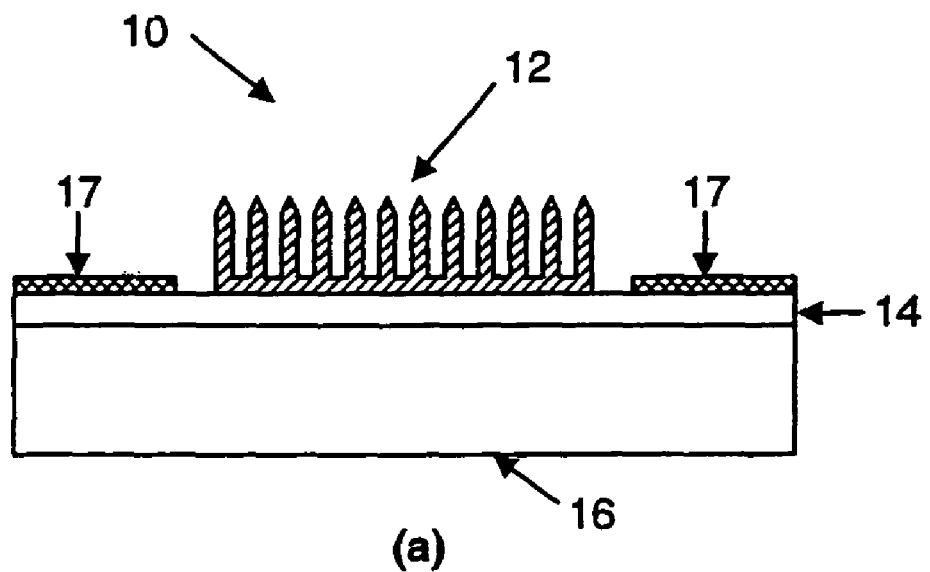
FIG. 1 (a) shows a schematic of a vertical cross-section view of the device structure for the conductivity-based ZnO nanotip biosensor.
Figure 1:
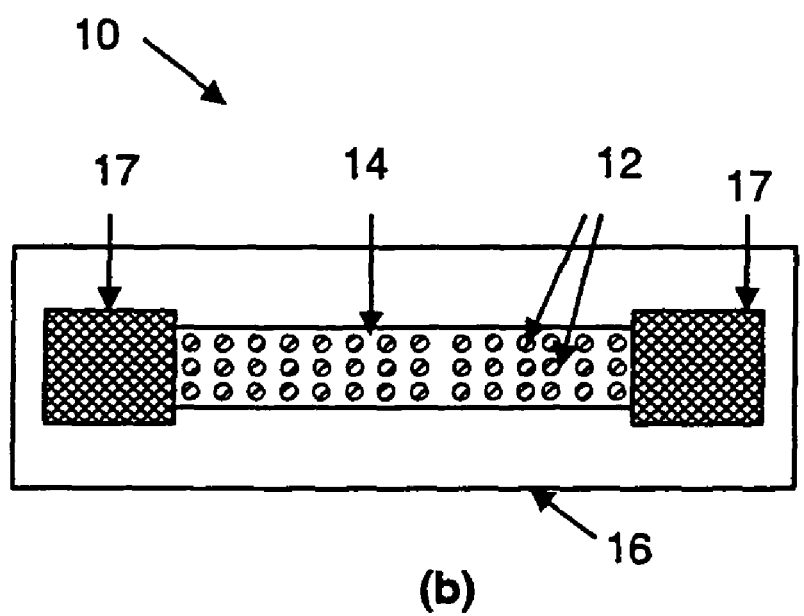

A biosensor is a device which is capable of providing analysis of various analytes or biomolecules using biological recognition elements which are combined with a signal transducer. Generally, the sensor will produce a signal that is quantitatively related to the concentration of the analytes.

The biological recognition elements serve to recognize the analytes. These elements include enzymes, microorganisms, tissues, antibodies, receptors, nucleic acids, organelles or whole cells.

Transducers are physical components of the biosensor that respond to the products of the biosensing process and outputs the response in a form that can be amplified, stored or displayed. Biosensing occurs only when the analyte is recognized specifically by the biological element. Biological recognition in vivo at a single cell level is characterized by high sensitivity, fast response, specificity and reversibility.

A "sensor surface" refers to the location upon which a binding partner is immobilized for the purpose of measuring changes in physical properties, such as optical refractive index, electrical conductivity, mass loading, etc. They include, but are not limited to, semiconductor, metal and dielectric surfaces.

ZnO is a wide bandgap semiconductor having a direct bandgap of 3.32 eV at room temperature and can be made semiconducting, piezoelectric, ferroelectric, ferromagnetic, and transparent and conducting through proper doping. ZnO has an exciton binding energy of 60 meV. It is found to be significantly more radiation hard than silicon (Si), gallium arsenide (GaAs), and GaN.

ZnO is a polar semiconductor with the (0002) planes being Zn-terminated and the (000$\bar{2}$) planes being O-terminated. These two crystallographic planes have opposite polarity and hence have different surface relaxations energies. This leads to a higher growth rate along the c-axis. The ZnO film grown on many semiconducting, insulating or metallic substrates have a preferred c-axis orientation normal to the surface. Therefore, ZnO growth results in a pillar like structure called ZnO nanotips on these semiconducting, insulating and metallic substrates, while ZnO grown on R-plane sapphire substrates results in a smooth epitaxial film. The ZnO nanotips can be grown at relatively low temperatures, giving ZnO a unique advantage over other wide bandgap semiconductor nanostructures, such as GaN and SiC.

ZnO is an important multifunctional material, which has wide applications in telecommunications, chemical and biochemical sensors and optical devices. In this application, ZnO nanotips are used as the sensor surface to enhance the immobilization in detection of DNA, protein, and harmful biological agents in the field of biological and biochemical sensors. The use of ZnO nanotip arrays also greatly increases the effective sensing area of the biosensor devices as will be described in greater detail below.

ZnO nanotips can be grown on various substrates. They can also be selectively grown on patterned layers of materials through substrate engineering. Both cases have been disclosed in U.S. patent application Ser. No. 10/243,269.

Referring to FIGS. 1a and 1b, a schematic of vertical cross-section view and a top view respectively of a conductivity-based ZnO nanotip biosensor 10 are shown. The biosensor consists of a substrate 16, a conductive thin film 14, a ZnO nanotip array 12 on the conductive thin film 14, and metal electrode pads 17. A reaction between the immobilized species on ZnO nanotips 12 with the target will result in a change in the total change accumulated on nanotips. This change will cause a transient current across the biosensor device, which will be used as the sensor output, as will be described below.

The substrate 16 can be a semiconductor substrate, such as Si or GaAs, in which case the biosensor can be integrated with electronic integrated circuits (ICs). In a second embodiment of the invention, the substrate 16 can be a transparent insulating substrate, such as glass or sapphire, in which case both electrical and optical sensing mechanisms can be used to realize a multifunctional sensor. In a third embodiment of the invention, the substrate 16 can be a piezoelectric substrate, such as quartz or lithium niobate ($LiNbO_3$), in which case the conductivity-based sensor can be integrated with the SAW-based sensor to realize another type of multifunctional sensor as described later in this application.

The conductive thin film 14 has certain conductivity, and it can be a semiconductor, such as Si with properly designed doping level, a metallic thin film, such as gold (Au), a transparent conductive oxide, such as indium tin oxide (ITO), or even the multilayer thin film. The thin film and the metal bond pads are deposited on the substrate 16, then patterned using the standard microelectronic processing techniques.

The ZnO nanotips 12 can be deposited on the substrate 16 and thin film 14 using the technology, but not limited to, metal-organic chemical vapor deposition (MOCVD), then patterned by the standard photolithography and etching process.

These ZnO nanotips serve as DNA or protein molecule binding sites. In other words, the ZnO nanotips 12 are preferably bonded with protein or DNA molecules to make conductivity-based biosensors, as will be described in detail below. Specifically, the conductive thin film 14 surface, with ZnO nanotips 12 grown on the top, will be designed and fabricated as conductivity-based biosensors. Preferably a probe is attached to said tip to seek the targeted molecule due to bioreaction. The probe may preferably be attached on a binding site or a target molecule preferably has a probe. Any useful probes preferably such as chemiluscence, fluorescence, etc. The dimensions of the conductive pattern, the aspect ratio and doping level of the ZnO nanotips, are optimized to enhance the sensitivity. Due to depletion or accumulation of carriers in the nanotips as a result of bioreactions, the conductance of the patterned tip arrays will change significantly. The depletion (accumulation) of the nanotips will result in a transient current across the line. The amplitude of this current will be a function of the amount of target material detected, and the duration to the reaction time. The similar effect was recently demonstrated using Boron doped silicon nanowire biosensors for detection of protein-protein interactions by Y. Cui, Q. Wei, H. Park, and C. M. Lieber, "Nanowire nanosensors for highly sensitive and selective detection of biological and chemical species", *Science* 293, 1289 (2001).

If a transparent substrate, either insulating or piezoelectric, is used, the conductivity based ZnO nanotip biosensor 10 can be operated in optical mode simultaneously with the conductivity mode. ZnO has an optical cut-off wavelength of approximately 373 nm at room temperature. This optical cut-off wavelength can be extended by using its ternary compound, magnesium zinc oxide ($Mg_xZn_{1-x}O$). As $Mg_xZn_{1-x}O$ is transparent down to ~240 nm (for x=0.6), the changes in the optical absorption characteristics before and after the bioreactions can also be detected and analyzed. During operation, the device is illuminated with ultra-violet (UV) light from one side (top or bottom), and the light is detected on the other side. Changes in the UV absorption spectra are unique to each chemical, allowing identification of the reactant species. Furthermore, if the tip array is coated with a thin layer of Au (<100A), it can also be functional for fluorescence biosensing as shown by V. H. Perez-Luna, S. Yang, E. M. Rabinovich, T. Buranda, L. A. Sklar, P. D. Hampton, and G. P. Lopez, "Fluorescence biosensing strategy based on energy transfer between fluorescently labeled receptors and a metallic surface", *Biosens Bioelectron.* 17, 71 (2002).

In another embodiment of the present invention, there is disclosed a second type of device, which is a ZnO nanotip-gate field-effect-transistor (FET). FETs have been used for chemical sensors. In a FET, a voltage bias applied to the gate of a FET will modulate the current flowing between its source and drain. There are two major types FETs which can be used with biosensors. The first is a metal-insulator-semiconductor FET (MISFET), composed of a metal gate deposited on a gate insulator layer, which is deposited on the semiconductor. The second is a metal-semiconductor FET (MESFET), composed of a metal gate directly deposited on the semiconductor. If the gate insulator is specifically an oxide, the MISFET device is known as a metal-oxide-semiconductor FET (MOSFET).

An FET type of biosensor can be realized by depositing ZnO nanotips on the gate region of the FET. Such an FET can be a current existing Si MOSFET, GaAS MESFET, etc. The surface charge changes occurring with the target on the ZnO nanotips will result in a potential difference between the gate and the substrate, and modulate the current flowing between the source and the drain. Unlike the resistor-type conductivity-based sensor described above, the FET type sensor can be used for both transient and steady-state current measurements, making it a more flexible device.

Figure 2:
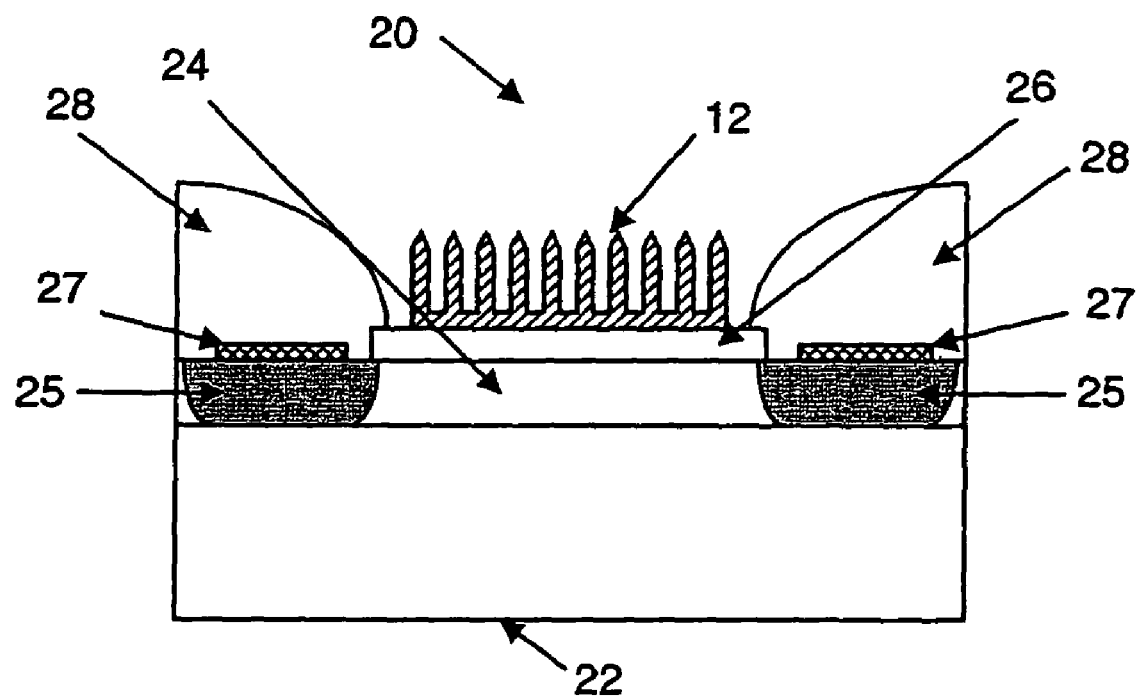
FIG. 2 shows a schematic of a vertical cross-section of a ZnO nanotip gate metal-insulator-semiconductor field effect transistor (MISFET).

More specifically, a novel transparent FET sensor is composed of a ZnO nanotip gate and a ZnO FET. Referring to FIG. 2, there is shown a schematic of a vertical cross-section view of nanotip gate ZnO MISFET biosensor 20. It is composed of a R-plane sapphire (R—$Al_2O_3$) substrate 22, a semiconductor ZnO thin epitaxial layer as a channel 24, doped ZnO source and drain regions 25, a gate insulator 26, metal electrodes 27 to the source and drain regions 25, the ZnO nanotips 12 deposited on the gate, and an encapsulation layer 28 to protect the device except the nanotip gate area.

In this device, $n^+$-ZnO 25 regions serve as the source and the drain. When Al is used for the metal contacts 27, it will heavily dope the ZnO thin film 24 under it, resulting in good non-alloyed ohmic contact as developed in H. Sheng, N. W. Emanetoglu, S. Muthukumar, and Y. Lu, "Non-alloyed Ohmic Contacts to $Mg_xZn_{1-x}O$", *J. Electronic Materials,* 31 (2002). This process will be used to simultaneously dope the source and drain regions and form their ohmic contacts in the ZnO MISFET structure. A thin insulation layer 26 will be deposited, and patterned on top of the n-ZnO 24 thin film. Candidate insulators 26 include, but are not limited to, silicon dioxide ($SiO_2$) and magnesium zinc oxide ($Mg_xZn_{1-x}O$) with more than 50% Mg mole percentage composition. The device will be protected with the encapsulating layer 28 from the chemical environments it operates in. The ZnO nanotips 12 will be grown on the insulator layer 26, patterned and etched to serve as the nanotip-gate.

The operation of the ZnO nanotip-gate transparent MISFET 20 is simple. When a biological reaction occurs with the target at the ZnO nanotips 12, the negative surface charge will change, inducing with a potential difference between the gate and the ZnO film. This potential difference will change the conductivity in the n-type ZnO channel 24 under the gate insulator 26, resulting in a change in the current between the source and the drain regions 25.

As in the conductivity-type ZnO nanotip biosensors 10 described above, the ZnO nanotip-gate transparent MISFET biosensor 20 can be operated in optical mode simultaneously with electrical mode. ZnO nanotips, R—$Al_2O_3$, $SiO_2$ and $Mg_xZn_{1-x}O$ (0.5<x<1) are all transparent to visible light, therefore allow the sensor to be operated in optical mode.

Figure 3:
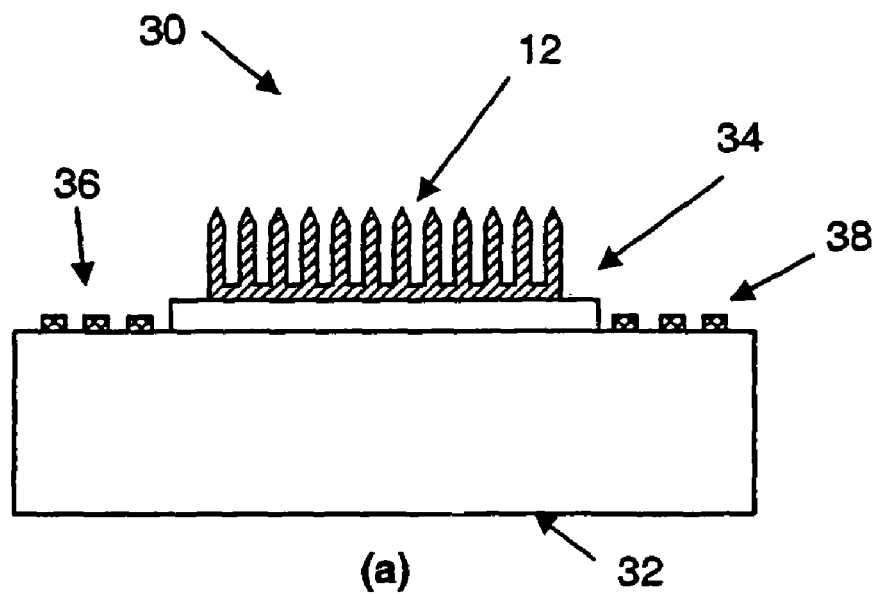
FIG. 3 (a) shows a schematic of a vertical cross-section view of a ZnO nanotip SAW sensor.
Figure 3:
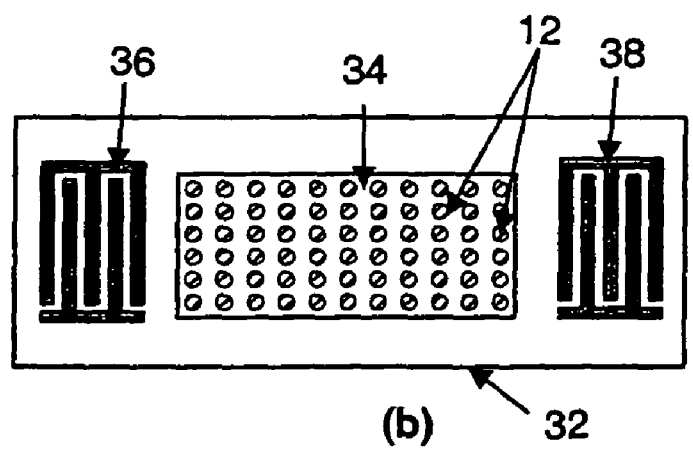

In another embodiment of the present invention, there is disclosed a third type of device which integrates piezoelectric ZnO nanotips with SAW biosensors. Referring to FIGS. 3a and 3b, there is shown a schematic of a vertical cross-section view and a schematic of a top view respectively of ZnO nanotip SAW biosensor 30. The ZnO nanotip SAW biosensor is composed of a piezoelectric substrate 32, an insulating amorphous layer 34, a metal input interdigital transducer (IDT) 36, a metal output IDT 38, and the ZnO nanotips 12.

The piezoelectric substrate 32 can be, but is not limited to, quartz, $LiNbO_3$, lithium tantalate ($LiTaO_3$), etc. An insulating amorphous layer 34 is deposited on the piezoelectric substrate and patterned using the standard microelectronic processing techniques. This insulating amorphous layer can be, but is not limited to, $SiO_2$ or $Si_3N_4$.

The ZnO nanotips 12 are deposited on the surface of the insulating layer 34 using MOCVD, or other deposition technology, then patterned and etched to define the nanotip coverage area. The metal IDTs 36 and 38 are then deposited and patterned using standard microelectronic processing techniques. The metal of choice is Al, but other metals can also be used.

The ZnO nanotip SAW sensor device 30 operates similarly to a planar SAW biosensor. A dualchannel biosensor consisting of two identical devices, one without target coating serving as the reference and the other with target coating serving as the sensor, are used together. As the target binds with the ZnO nanotips 12 on the sensor device, mass loading of the sensor will result in a decrease of the phase velocity under the ZnO nanotips. This will results in a phase difference between the output signals of the reference and the sensor devices. The use of ZnO nanotips dramatically enhances the immobilization of DNA, protein and other small biomolecules, therefore the sensitivity of the biosensors. Our preliminary experimental results demonstrate that the immobilization rate of ZnO nanotips is over thirty times higher than that of smooth surface. It is well known that the rough surface will increase the viscosity of the sensing media on the acoustic path and deteriorate the device performance. Therefore, the ZnO nanosize tip-type structures 12 will have higher electromechanical coupling coefficient to compensate the increased propagation loss as disclosed by K. K. Zadeh, A. Trinchi, W. Wtodarski, and A. Holland, "A novel love-mode device based on a ZnO/ST-cut quartz crystal structure for sensing applications", *Sensors and Actuators A* 3334, 1 (2002).

In the refinement of the invention, the SAW based ZnO nanotip biosensor 30 can be operated in optical and SAW modes simultaneously, if a transparent piezoelectric substrate, such as quartz or $LiNbO_3$, is used. As in the conductive-type nanotip biosensors 10, the sensor 30 is illuminated with UV light on one side (either top or bottom) and the transmitted UV light is detected at the other side. The UV absorption spectrum can be used to identify the reactant species.

In another refinement of the invention, the SAW based ZnO nanotip biosensor 30 can be operated in electrical and SAW modes simultaneously, if the insulating layer structure is replaced with the resistor-type conductive ZnO nanotip biosensor structure.

In a further refinement of the invention, the ZnO nanotips 12 can be combined with the monolithically integrated tunable SAW (MITSAW) sensors disclosed previously (U.S. Pat. No. 6,559,736 and U.S. patent application Ser. No. 09/905, 205), to enhance their performance.

In preliminary work, SAW delay lines are fabricated on 128° Y-cut LiNbO$_3$ with a ZnO nanotip/SiO$_2$ layer structure deposited on the propagation path. The IDT structure of this prototype device consists of 50 pairs of electrodes, 963 µm long, 3 µm wide and 3 µm apart from each electrode for both IDTs. The phase velocity (v) of the SAW on the 128° Y-cut LiNbO$_3$ is 3668 m/s, and the wavelength (λ) of the test pattern is 12 µm. From the equation $f_c=v/\lambda$, the expected center frequency is 305 MHz. The bandwidth is $BW_{3db}=(0.9/N_p)*f_c=0.9*305/50=5.49$ MHz. On the propagation path of the prototype devices, the sensor region has 600 nm ZnO nanotip/100 nm SiO$_2$ is 1116 µm long and 594 µm wide. Furthermore, the dual channel (reference and sensor channels) device is tested using an Agilent 8573D Network Analyzer. The reference channel has no protein bonding and the sensor channel is bonded with 100 ng protein on the ZnO nanotip over an area of 6.629☐10$^{-3}$ cm$^2$.

Figure 4:
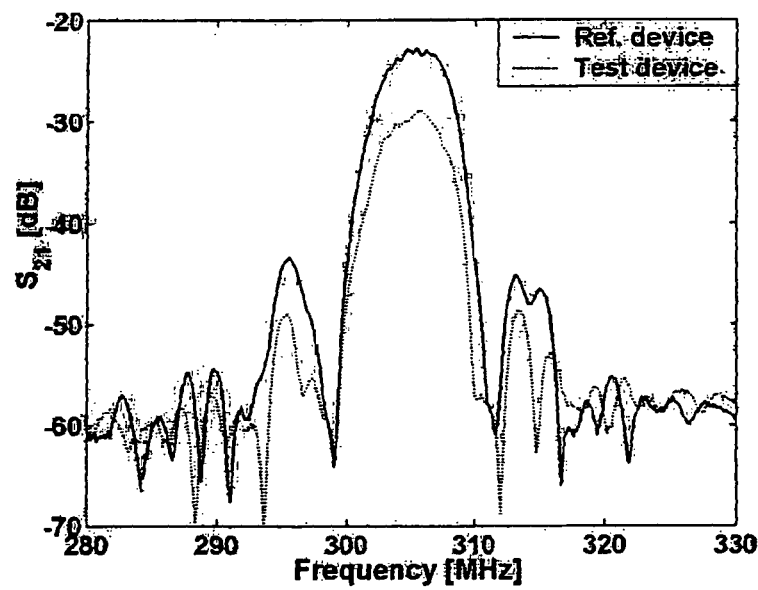
FIG. 4 (a) shows an example of transmission spectra as a function of frequency for test ZnO nanotip SAW sensor devices.
Figure 4:
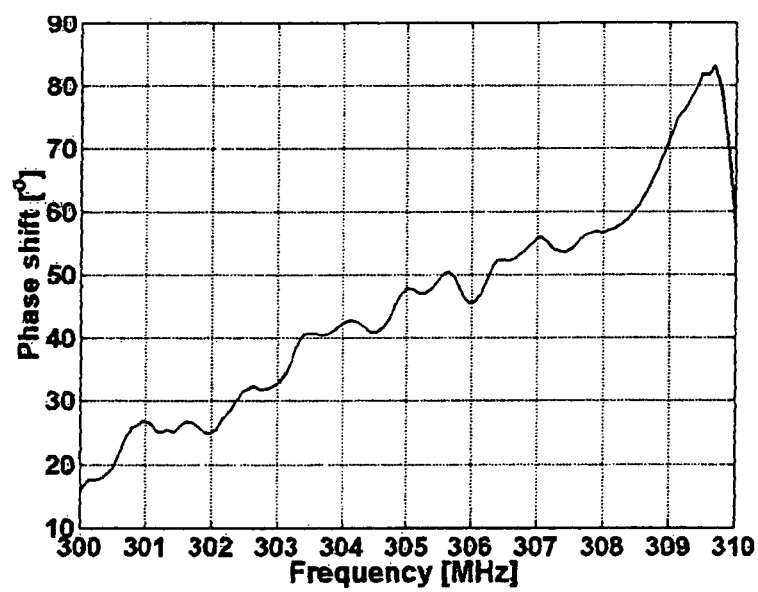

The frequency responses of the reference sensor device and the actual test sensor device are shown in a graph shown in FIG. 4a. The X-axis is the frequency and the Y-axis is the S$_{21}$ transmission spectra of reference and sensor device. As shown in FIG. 4a, the sensor device has a shift to lower frequency compared with the reference device. An additional insertion loss of 6.14 dB is observed for the protein bonded sample. However, the insertion loss shift depends on a number of factors, and by itself is not a good sensing mechanism. Instead, the phase shift of the signal is preferred for accurate and repeatable measurements.

FIG. 4b shows a graph displaying a phase difference between the reference and sensor prototype devices. The X-axis is the frequency and Y-axis is the phase difference between the reference and sensor device. As shown in FIG. 4b, the sensor device has a 47.68° phase shift at the center frequency 305 MHz compared with the reference device. The phase shift increases with increasing frequency, due to the different velocity dispersion characteristics of the SAW propagating in the reference and sensor channels. The phase velocity decreases with increasing frequency, as sensitivity increases with frequency. This phase velocity decrease results with a larger phase difference between the sensor and reference devices with increasing frequency. Nominally, the phase shift should be a monotonically increasing function. However, due to such factors as electromagnetic feedthrough and triple transit interference (TTI), the phase response has ripples. The impact of these secondary effects on sensor performance can preferably be minimized. The proof-of-concept device uses an unoptimized SAW delay line structure. Narrower bandwidths and larger phase shifts can be achieved by optimizing the device parameters and proper choice of substrate.

Figure 5:
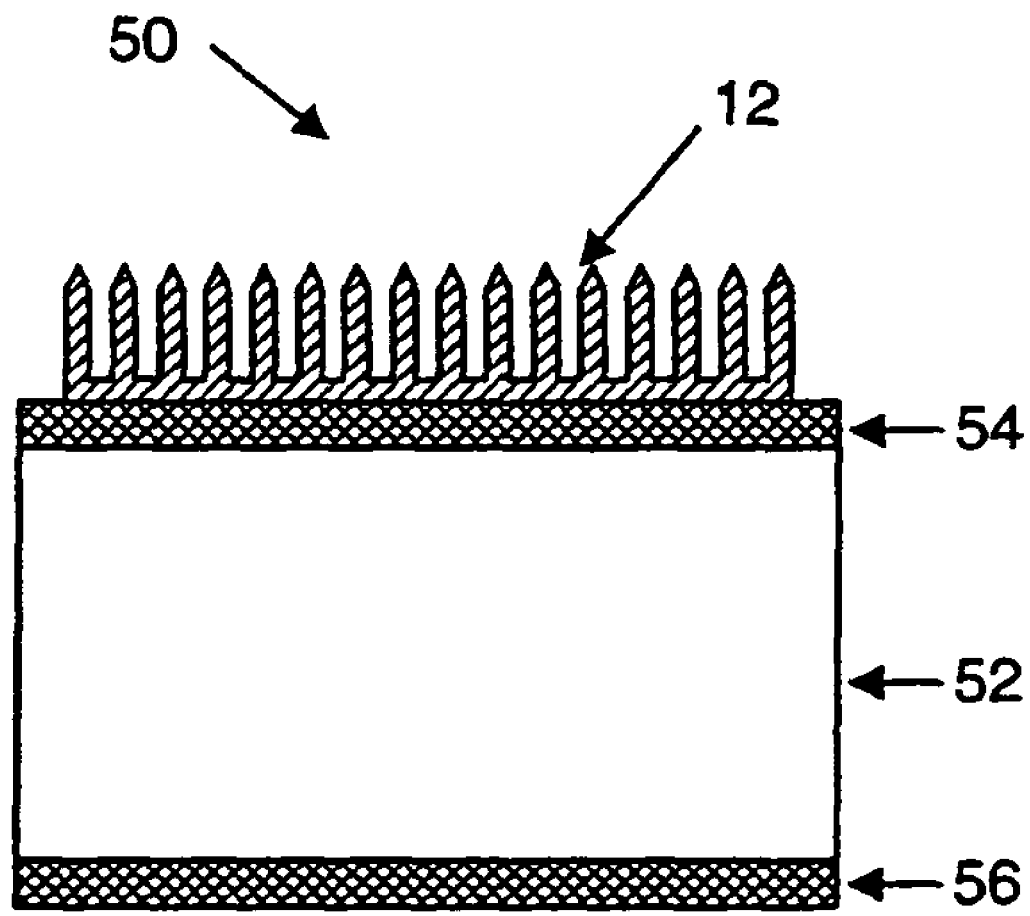
FIG. 5 shows a schematic of a vertical cross-section of a ZnO nanotip BAW sensor.
Figure 6:
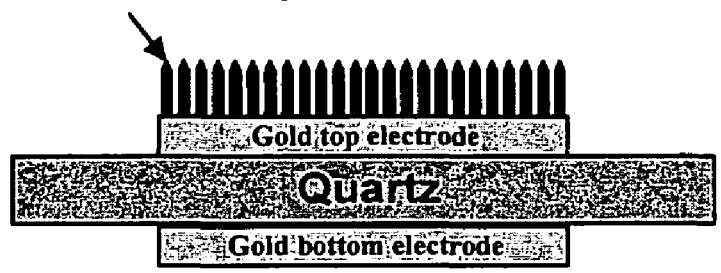
FIG. 6 shows a Schematic cross-section of ZnO nanotip QCM sensor.

In another embodiment of the present invention, there is disclosed a fourth type of device which integrates piezoelectric ZnO nanotips with BAW biosensors. Referring to FIG. 5, there is shown a schematic of a vertical cross-section view of a ZnO nanotip BAW biosensor 50. The ZnO nanotip BAW biosensor 50 is composed of a piezoelectric material 52, a metal top electrode 54, a metal bottom electrode 56 and ZnO nanotips 12.

The piezoelectric material 52 can be, but is not limited to, quartz, LiNbO$_3$, LiTaO$_3$, etc. The metal top 54 and bottom 56 electrodes are deposited and patterned using the standard microelectronic processing techniques.

The ZnO nanotips 12 are deposited on the top metal electrode surface using MOCVD, or other deposition technology, and then patterned and etched to define the nanotip coverage area of the BAW sensor.

In a further embodiment of the ZnO nanotip BAW sensor 50, the center area of the top surface of the piezoelectric substrate is not metallized. The ZnO nanotips 12 are deposited on the bare piezoelectric substrate surface 52, so that the top metal electrode 54 surrounds, but does not contact the ZnO nanotips 12.

The ZnO nanotip BAW sensor 50 operates similarly to a BAW resonator device. The BAW resonator will resonate at a specific frequency determined by the piezoelectric substrate material properties and thickness. When bonding of the target occurs on the ZnO nanotips 12, mass-loading results with a shift in the resonance frequency of the resonator, directly proportional to the amount of target material bonded to the ZnO nanotips 12.

In a further embodiment of the ZnO nanotip BAW sensor 50, the crystal resonator of FIG. 5 can be replaced with a thin film resonator structure, including, but not limited to, air gap resonators, solidly mounted resonators and membrane (Film Bulk Acoustic Resonator or FBAR) resonators. The thin film resonator structure includes, but not limited to, an air-gap structure on top surface of the substrate, a membrane structure on the substrate and an acoustic mirror on top surface of the substrate.

In a further embodiment of the present invention, there is disclosed a biochip consisting of ZnO nanotip array as biosensors to simultaneously detect a number of different biological information. For certain clinical and scientific applications it is desirable to use multiple biosensors on a chip for simultaneous detection of several biomolecular targets. For this purpose a biosensor chip having multiple detection units for different targets. As described above, both types of biosensor devices with 1D or 2D arrays on a chip can be fabricated through regular microelectronics fabrication processes.

The current invention presents a new biochemical sensor technology with high sensitivity and multimodal operation capability. The sharp ZnO nanotips 12 on four type devices, as discussed above, provide the favorable binding sites to enhance the immobilization, and increase the effective sensing area, therefore, improve the sensing and detection efficiency. The changes in electrical conductivity, or/and optical absorption, or/and fluorescence in conductive and semiconductive ZnO nanotips will be used to sense the targeted biochemical reactions. The ZnO nanotip SAW or BAW sensors possess both the advantages of SAW or BAW, and nanostructured biosensors.

The ZnO biosensors described above are used to detect RNA-DNA, DNA-DNA, protein-protein, protein-DNA, and protein-small molecule interactions taking advantage of the enhancement of immobilization of DNA, protein molecules on the ZnO nanotips. The optimum immobilization conditions can be used for the biosensors to further enhance their sensitivities and specify the target molecules.

For DNA immobilization, a solution of avidin is applied to the clean surface of ZnO nanotips 12, and then biotinylated oligonucleotide will be attached to the modified nanostructured surface as disclosed by G. Marrazza, I. Chianella, and M. Mascini, "*Disposable DNA electrochemical sensor for hybridization detection*", Biosens Bioelectron. 14, 43 (1999).

The modified nanostructured surface includes the ZnO surface 12 initially coated with Cr, Ti, etc., to help the subsequent Au layer wet the surface. The Au film is then deposited and modified with thiol/dextran, which in turn will allow the covalent attachment of avidin as disclosed by S. Tombelli, M. Mascini, L. Braccini, M. Anichini, and A. P. Turner, "*Coupling of a DNA piezoelectric biosensor and polymerase chain reaction to detect apolipoprotein E polymorphisms*", Biosens Bioelectron. 15, 363 (2000). Thiolated DNA oligonucleotides are covalently attached to mercaptosilane-derivatised surface via succinimidyl 4-[malemido-phenyl]butyrate (SMPB) crosslinker as disclosed by T. A. Taton, C. A. Mirkin, and R. L. Letsinge, "*Scanometric DNA array detection with nanoparticle probes*", Science 289, 1757 (2000) and L. A. Chrisey, G. U. Lee, and C. E. O'Ferrall, "*Covalent attachment of synthetic DNA to self-assembled monolayerfilms*", Nucleic Acids Res. 24, 3031 (1996). The Thiolated DNA oligonucleotides can serve as the biological recognition elements which recognize the analytes.

For testing the efficiency of DNA immobilization procedures, model oligonucleotides with a radioisotope/fluorescent label are preferably used. For testing and calibration of DNA/RNA ZnO nanotip biosensors, a series of complementary pairs of oligonucleotides (20 and 50 nucleotides in length) which are 30, 50 and 70% GC-reach are synthesized having different percents of complementarity (from no to several mismatches). Basically, preferably light with a particular wavelength ($\lambda$) is passed through the transparent ZnO nanotip 12 and one member of each pair of oligonucleotides is immobilized on a surface of ZnO biosensor 10 and the device is tested in a series of hybridization experiments with the corresponding targets. Different hybridization conditions, as well as different RNA targets are evaluated. These targets may preferably be labeled. As an example of the practical application two sets of experiments are conducted with specific targets. One such target is detection of cold-shock inducible cspA mRNA from *E. coli*. Some major advances in understanding of the regulatory mechanisms of cspA expression have been made as disclosed by S. Phadtare, J. Alsina, and M. Inouye, "*Cold-shock response and cold-shock proteins*", Curr Opin Microbiol. 2, 175 (1999). Another is detection of mutations in the BRCA1 gene. This gene is responsible for 40% of breast cancer cases and 80% of breast-ovarian cancer cases as disclosed by M. O. Nicoletto, M. Donach, A. D. Nicolo, G. Artioli, G. Banna, and S. Monfardini, "*BRCA-1 and BRCA-2 mutations as prognostic factors in clinical practice and genetic counseling*", Cancer Treat. Rev. 27, 295 (2001). We preferably use oligonucleotides complementary to the 185delAG and 188del11 mutations of *the* gene, which are the most common in all reported cases as disclosed by D. Tong, M. Stimpfl, A. Reinthaller, N. Vavra, S. Mullauer-Ertl, S. Leodolter, and R. Zeillinger, "*BRCA1gene mutations in sporadic ovarian carcinomas: detection by PCR and reverse allelespecific oligonucleotide hybridization*", Clin. Chem. 45, 976 (1999). So, if we see binding, i.e. we get a signal such as fluorescent light, we know that patient's DNA strength hits breast cancer mutation.

For protein immobilization, strategies similar to those of DNA are used. As mentioned above, proteins may have strong affinity to ZnO surface 12. The Au coated ZnO surface is modified with thiol/dextran and activated by N-hydroxysuccinimide and N-(3-dimethylaminopropyl)-N-ethylcarbodiimide allowing covalent attachment of the protein as disclosed by N. Barie and M. Rapp, "*Covalent bound sensing layers on surface acoustic wave (SAW) biosensors*", Biosens Bioelectron 16, 979 (2001). The ZnO surface 12 will be precoated with polyethylenimine and the protein will be crosslinked to the surface via glutaraldehyde as disclosed by J. Ye, S. V. Letcher, and A. G. Rand, "*Piezoelectric biosensor for the detection of Salmonella typhimurium*", J. Food Sci. 62, 1067 (1997). Also bromocyano-immobilization will be preferably modified in which the shielding layer (polyimide or polystyrene) will be first loaded on the ZnO surface 12, following CNBr activation and coupling the protein as disclosed by T. Wessa, M. Rapp, and H. J. Ache, "*New immobilization method for SAW-biosensors: covalent attachment of antibodies via CNBr*", Biosens Bioelectron 14, 93 (1999).

In another case, for protein immobilization, a histidine kinase called EnvZ was used. The protein was first phosphorylated with $\gamma$-[$^{32}$P] ATP and solution of $^{32}$P-labeled EnvZ was loaded on the nanotips grown on a square glass plate (5×5 mm). After incubation for 90 minutes, plates were washed extensively at room temperature by changing the washing buffer solution five times. The radioactivity of the plate was then measured. More than 90% of the protein was retained on the surface, indicating a strong affinity of the protein to the ZnO surface. It was also found that EnvZ attached on the nanotip surface retained its biochemical property, as approximately 80% of $^{32}$P radioactivity was released when the plate was incubated in a solution containing OmpR, an EnvZ substrate, but no radioactivity was released in the presence of other proteins. This model system is preferably used for analysis of protein-protein interactions via optical techniques, since EnvZ forms a stoichiometric complex with OmpR.

Fluorescence resonance energy transfer (FRET) is a quantum mechanical process wherein excitation energy is transferred from a donor fluorophore to an appropriately positioned acceptor positioned acceptor fluorophore without emission of a photon. Energy can be transferred this way only over a very limited distance, and the efficiency of the energy transfer varies inversely with the sixth power of the distance separating the donor and acceptor. One of the most important uses of FRET spectroscopy is to study protein-protein interactions.

For testing protein immobilization in addition of a histidine kinase we use preferably as a model, calmodulin (CaM) fused with two mutant proteins, CFP (a mutant of green fluorescent protein, GFP; cyan fluorescent protein) at the N-terminal end and YFP (another mutant of GFP; yellow fluorescent protein) at the C-terminal end as disclosed by A. Miyawaki, J. Llopis, R. Heim, J. M. McCaffery, J. A. Adams, M. Ikura, and R. Y. Tsien, "*Fluorescent indicators for Ca2+ based on green fluorescent proteins and calmodulin*", Nature 388, 882 (1997). This allows us to easily determine concentration of the protein by measurement of fluorescent intensity. Moreover, CaM protein is termed "cameleon", since it responds to $Ca^{++}$ causing FRET (fluorescence resonance energy transfer) as mentioned above. It is critical to observe whether $Ca^{++}$ is close enough to calmodulin (CaM), in order for them to interact. Again, preferably light with a particular $\lambda$ (i.e. light capable of exciting the GFP) is passed through transparent ZnO nanotip 12. If the green fluorescent protein fluoresces at its characteristic $\lambda$, there is no protein interaction since the protein distance is greater than a specific amount and therefore no FRET occurs. However, if the calmodulin and $Ca^{++}$ are close enough (within FRET proximity) to interact, the GFP is excited but does not emit a photon. Preferably, a sensitized emission from $Ca^{++}$ occurs, so FRET occurs. The effect can be monitored directly on the ZnO sensor 10. Since the ZnO film is transparent, the cameleon-bound ZnO film can be excited from the bottom and the intensity of the emission spectra recorded. The use of cameleons allows us to evaluate the ZnO sensor 10 performance preferably by two mechanisms such as electrical (conductivity) and optical (fluorescence), or acoustic (SAW) and optical (fluorescence). The FRET method monitors real-time protein-protein interaction and/or conformational changes. Therefore, the comparison of our acoustic wave/conductivity measurements with FRET data helps to evaluate signal responsiveness.

The ZnO DNA and protein nanotip array based sensors in this application will further benefit to explore genome-wide gene expression for molecular diagnostics, drug target discovery, and validation of drug effects. The ZnO nanotip-based biosensors can also be applied to development of new methods for the prevention, diagnosis and treatment of diseases. Furthermore, the application of ZnO and its nanostructure-based biosensors can be extended to detection of toxic biochemical agents and hazardous chemicals against bioterrorism and environmental monitoring and protection. Unlike other sensor technologies, ZnO biosensors can operate in multimodes due to its multifunctional material properties (semiconductor, piezoelectric, transparent and conductive, etc.). Nanotips made from ZnO and its ternary compound can be used for UV absorption and fluorescence detection. ZnO nanotip arrays can be highly dense for diagnostic kits and flow-through systems, including ZnO UV biotesting bench (containing emitters, detectors, modulators, and filters), gene chip, lab-on-a chip and living-cell chip.

In a further alternate refinement of the present invention, there is provided two types of ZnO nanotip based sensors, which integrate piezoelectric ZnO nanotips with QCM and with TFBAR, respectively.

The QCM is a sensitive thickness monitor used in a variety of technological applications. It is also a versatile research tool for chemical sensor, nanotribology, wetting transition, and superfluid transition studies. Due to its high-quality (Q) factor, typically 10,000 to 100,000 at room temperature, it is a powerful device in a variety of technological applications and a versatile tool in a number of research fields. By growing ZnO nanotip on the top of the conventional gold electrodes, the effective adsorbing surface area and hence sensitivity will be significantly enhanced with no sacrifice of the mechanical quality factor or the stability in the resonant frequency. When gases adsorbed onto a QCM, the resonant frequency f decreases proportionally to the mass changes:

$$\Delta f_{ad} = \frac{4f^2}{nZ_q} \frac{\Delta m}{A}$$

where $Z_q$ is the transverse acoustic impedance of the quartz, 8.863106 kg/m², n is the harmonic acoustic number (n=1, 3, 5 . . . ), and A is the geometric area of electrodes. When a crystal is dipped into a solution, the relationship between the f and Δm is no longer linear and corrections are necessary.

The coupling of the crystal surface to a liquid drastically changes the frequency when a quartz crystal oscillates in contact with a liquid; a shear motion on the surface generates motion in the liquid near the interface. The oscillation surface generates plane-laminar flow in the liquid, which causes a decrease in the frequency proportional to $(\rho\eta)^{1/2}$:

$$\Delta f = f_0^{3/2} \left( \frac{\rho\eta}{\pi\rho_q\mu_q} \right)^{1/2}$$

where ρ is the liquid density and η is the viscosity. FIG. 1 shows the device structure for QCM sensor with ZnO nanotips deposited on the active area of the top electrode. QCM sensors are known to have a limitation in achieving a higher sensitivity due to their low-frequency operation, which is several hundred MHz, and they suffer from poor integration into arrays.

On the other hand, the thin film bulk acoustic resonator (TFBAR) has recently emerged as an attractive sensor device, as it can operate at much higher frequencies. TFBAR consists of a piezoelectric film sandwiched by a top and bottom electrodes. It has many advantages, such as small size, low insertion loss and lower power consumption. In addition, TFBAR sensors are much smaller, and can be readily integrated as arrays. The TFBAR sensors can be integrated with other Si-based electronic components on the same substrate and compatible with small-size microwave aerials, and hence can be used for wireless distance probing. The sensitivity $S_f$ of a TFBAR sensor due to the mass loading effect is calculated using the Sauerbrey's formula:

$$\Delta f = \frac{2f_0^2}{A\sqrt{c_{66}\rho}} \Delta m = S_f \Delta m$$

where $f_0$ is the reference resonance frequency and $f_0+\Delta f$ is the loaded frequency, $c_{66}$ is a stiffness constant of the piezoelectric material, ρ is its density.

Figure 7:
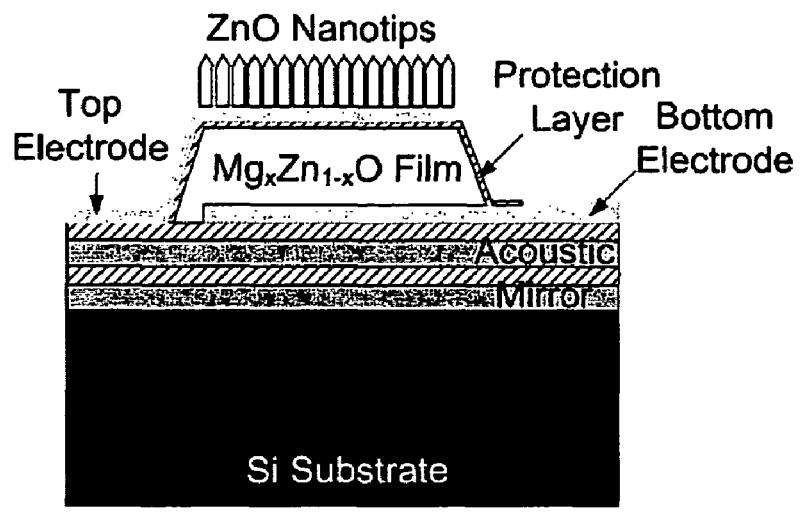
FIG. 7 (a)-(c) show the schematics of three types of TFBAR sensors integrated with ZnO nanotips.
Figure 7:
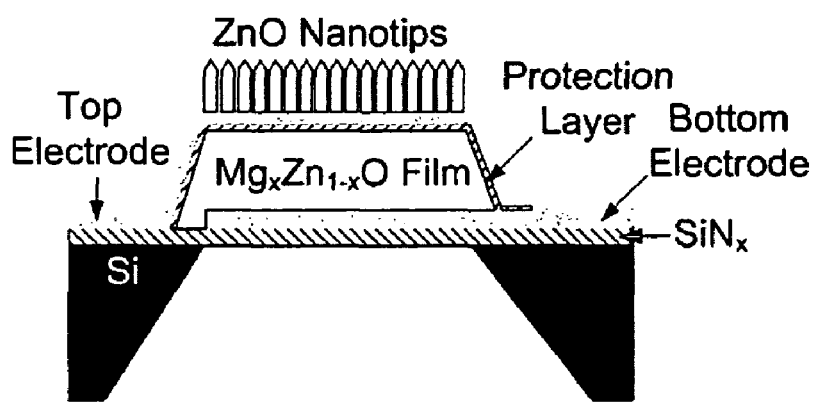
Figure 7:
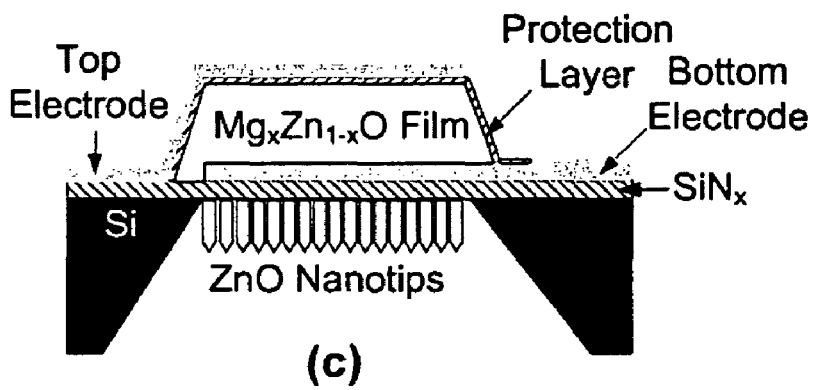

Turning now to FIG. 7 there is shown a schematic of three types of TFBAR sensors with ZnO nanotips. In FIG. 7 (a), a solidly mounted (SM) TFBAR is built on Si or GaAs substrate with an acoustic mirror. ZnO nanotips can be deposited on the top electrode. The acoustic mirror is comprised of quarter wavelength reflectors to isolate TFBAR from substrate, made of materials with a large acoustic impedance difference, such as SiO₂ and W. Therefore SM TFBAR is a low cost, easily manufacturable structure and is attractive for monolithic integration with Si or GaAs ICs.

FIGS. 7(b) and (c) show micromachined TFBAR with a backside substrate etched cavity structure by deep etching. In FIG. 7(b), ZnO nanotips are deposited on the top electrode. In contrast, ZnO nanotips are deposited on the bottom electrode. This structure can be integrated with microfluidic system.

Specifically in FIG. 7, there is shown schematics of vertical cross-sections of three types of TFBAR sensors (a) ZnO nanotips integrated with a solidly mounted TFBAR with an acoustic mirror; (b) micromachined TFBAR with ZnO nanotips grown on the top electrode; (c) micromachined TFBAR with ZnO nanotips grown in the cavity structure.

Experimental investigation of the ZnO-nanotip-based sensors according to the present invention has been conducted.

Figure 8:
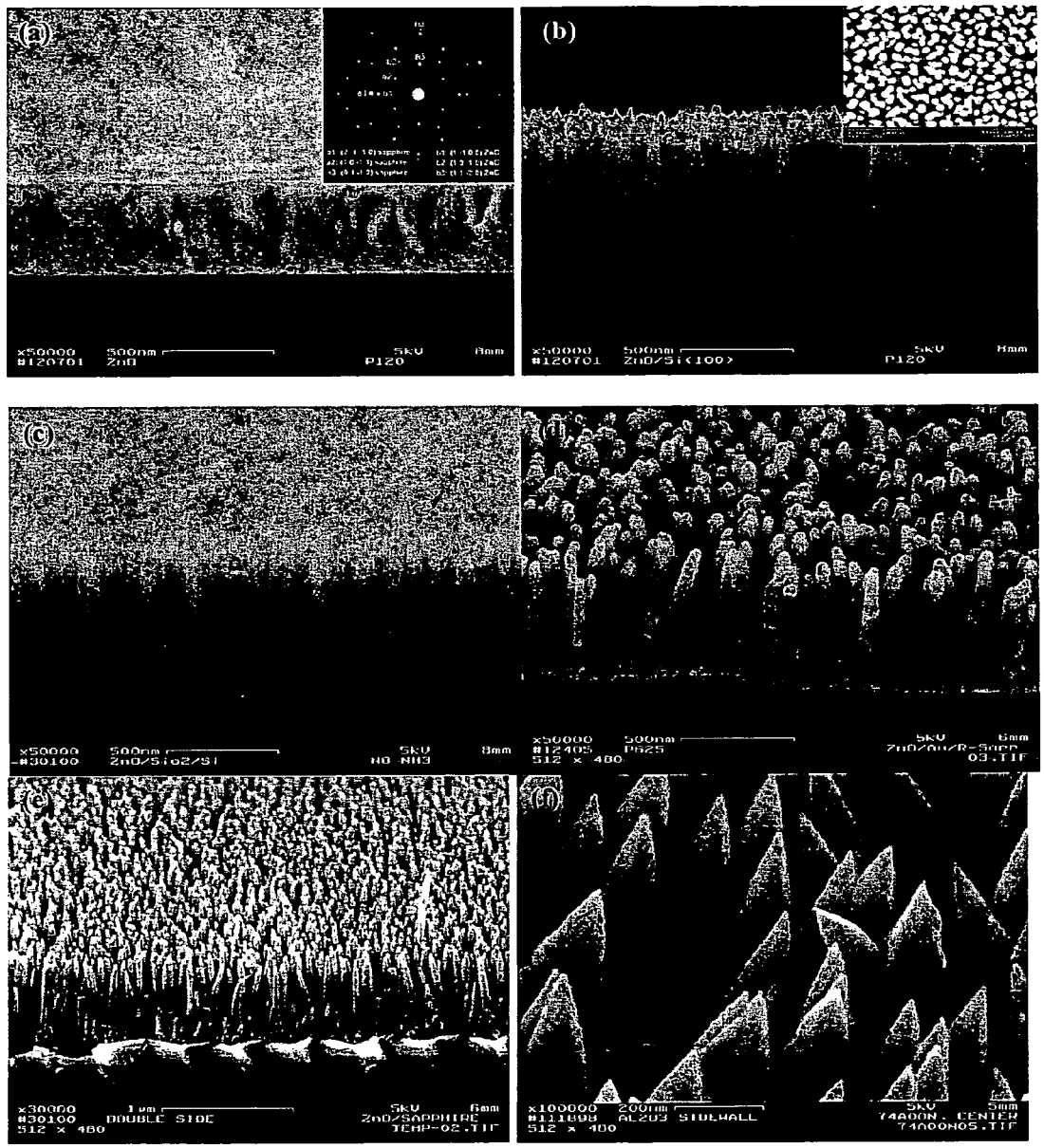
FIG. 8 (a)-(f) show the a-plane ZnO epitaxial film (a), and c-axis oriented ZnO nanotips (b)-(f) grown on various substrates using MOCVD.

Specifically with respect to ZnO nanostructures a preliminary investigation on the MOCVD growth of c-axis oriented ZnO nanotips has been conducted on various substrates, including c-plane sapphire (c-Al₂O₃), Si, fused silica, and metals (Au, Ti), as shown in FIG. 8 (b-f). FIG. 8. (a) shows ZnO films grown on r-sapphire substrates. The films show a flat morphology with the orientation relationship (11-20) ZnO||(01-12) Al₂O₃ and [0001] ZnO||[01-11] Al₂O₃. Therefore, the c-axis of ZnO lies in the plane of the substrate. By controlling the initial growth stage (nucleation vs. other growth mechanisms), ZnO nanotips with a high aspect ratio were obtained. The ZnO nanotip arrays are single crystalline, with uniform size and orientation, and show good optical quality. HRTEM analysis confirms the single crystalline quality of ZnO nanotips grown on amorphous substrates such as fused silica.

Turning to FIG. 8. there is further shown; (a) ZnO film epitaxially grown on R—Al$_2$O$_3$, the inset is the electronic diffraction pattern of ZnO and r-Al$_2$O$_3$ viewed along the [01$\bar{1}\bar{1}$] zone axis of Al$_2$O$_3$, indicating the excellent crystal quality; (b) ZnO grown on (100) Si with columnar growth, the width of the columns was measured to be ~60 nm using AFM, and the inset is the SEM top view. The growth conditions were same for both substrates. (c) ZnO columnar structures grown on a SiO$_2$/Si substrate, indicating that the crystallinity of Si does not influence the growth of these columns; (d) ZnO nanotips grown on Au; (e) ZnO grown on a c-Al$_2$O$_3$ substrate. Columnar growth of ZnO is observed with the c-axis perpendicular to the plane of the substrate; (f) a magnified image of the sharp ZnO nanotips grown on c-Al$_2$O$_3$.

Furthermore, with respect to ZnO nanostructure-based devices and processing technologies, experimental verification demonstrates a first high speed ZnO MSM UV photodetector [1], using epitaxial ZnO on r-Al$_2$O$_3$ in accordance with the present invention. The devices show high photoresponsitivity (400 A/W at 5V bias). The response speed (~1 μs) is much faster than published results (tens μs to hundreds of ms [2]) due to the high material quality. We have demonstrated the first ZnO Schottky diode [3], as well as the first ZnO Schottky photodetector [4] which has a fast photoresponse component with rise and fall times of tens of nanoseconds. The present invention also provides an optically addressed normal incidence high contrast UV modulator [5] that exploits the in-plane optical anisotropy in epitaxial ZnO on r-Al$_2$O$_3$. An ultra-fast dynamic polarization rotation of ~12□ and a high contrast ratio of 70:1 were achieved. ZnO thin film based SAW devices with piezoelectric coupling coefficients up to 6% in the ZnO/r-Al$_2$O$_3$ material system have been demonstrated [6]. The piezoelectric behavior of Mg$_x$Zn$_{1-x}$O was shown for the first time in SAW [7] and BAW [8] devices. The present invention can also be implemented to employ the ZnO/SiO$_2$/Si system for temperature compensated SAW filters integrated with ICs [9], and both alloyed [10] and non-alloyed [11] ohmic contacts to ZnO with low contact resistance. Further developments include a novel monolithically integrated tunable SAW chip technology, using ZnO/Mg$_x$Zn$_{1-x}$O heterostructures integrated on ZnO/r-Al$_2$O$_3$. The voltage controlled phase shift has been demonstrated. Turning to FIG. 7 there is shown a phase shift vs. bias voltage curve of the Sezawa (725 MHz) wave mode. In addition, a UV light tuned MITSAW device was realized [12]. It integrates the piezoelectric ZnO SAW with semiconductor ZnO UV sensor on the same chip, resulting in the unique advantage of desired frequency output for zero-power and wireless sensing.

Figure 9:
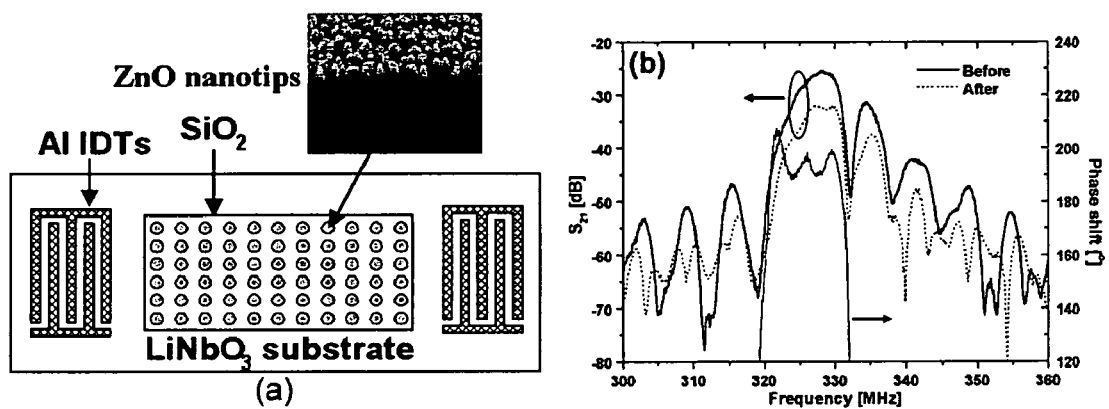
FIG. 9 (a) shows a schematic of the ZnO nanotip-based SAW biosensor structures with the inset showing the ZnO nanotips grown on the SAW channel.

A novel structure consisting of ZnO nanotips grown on a 128° Y-cut LiNbO$_3$ SAW delay line has been reported by Zhang et al. [12]. The ZnO nanotips were grown by MOCVD on the top of a SiO$_2$ layer which was deposited and patterned on the LiNbO$_3$ SAW delay path, as shown in FIG. 9. The ZnO nanotip arrays enhanced DNA immobilization by a factor of 200 compared to ZnO films with smooth surface. This device structure possesses the advantages of both traditional SAW sensors and ZnO nanostructures, and shows promising potential for portable sensors in biological and biomedical applications. During the DNA oligonucleotide immobilization test, when a 1 μg/μl DNA oligonucleotide solution was applied on the sensing channel, a 191° phase shift and 6.5 dB of additional insertion loss at the center frequency of 327.94 MHz was observed compared with the reference channel. In the radioactive test, 4.32□10$^2$ ng/cm$^2$ APE and 7.33□10$^2$ ng/cm$^2$ complementary DNA oligonucleotide were detected. In the SAW device test, the sensitivity to immobilization was calculated to be 2.2□10$^{-3}$ g/cm$^2$, while the sensitivity to the target second strand DNA oligonucleotide was 1.5□10$^{-3}$ g/cm$^2$.

Turning now FIG. 9 there is shown; (a) Schematic of the ZnO nanotip-based SAW biosensor structures, (b) S$_{21}$ (transmission) spectra from the sensor before and after DNA oligonucleotide immobilization. The phase shift at the center frequency of 327.94 MHz is 191°. The circle indicates the frequency responses of the SAW sensor before and after immobilization, with respect to the left axis, the insertion loss.

As a parallel development, a diode with n-type ZnO nanotips and p-Si substrate was fabricated with minimized thickness of the interfacial SiO$_2$ [14]. The electrical properties of the ZnO/Si heterojunction are investigated. ZnO nanotips are grown on HF-treated Si (100) substrate at ~480° C. with minimized oxygen exposure prior to initial growth. A ZnO nanotip mesa with diameter of ~200 μm is formed by wet etching ZnO nanotip layer down to the conductive p-Si substrate. ZnO nanotips are filled with diluted photoresist before the metal deposition to prevent the metal from reaching the bottom of the nanotips, which may result in the short circuit. 100 nm Al is deposited by E-beam evaporation to form ohmic contacts to ZnO nanotips and p-Si substrate, respectively. I-V characteristics of the diode indicate that the electron carriers can easily tunnel through the ZnO/Si heterojunction. The forward threshold voltage of the diode is measured to be below 2.0 volts. The forward current at 3.0 volts is 5.64 mA, and the reverse leakage current at 10 volts is 15 μA. The breakdown voltage of the diode is ~17 volts. This development gives an example how ZnO nanotips are integrated into Si-based electronics.

Directly related to the current invention, we have demonstrated the multi-mode Mg$_x$Zn$_{1-x}$O TFBAR on r-plane sapphire [8], consisting of Al/Mg$_x$Zn$_{1-x}$O/n$^+$ ZnO/r-sapphire structure. Al and n$^+$ ZnO served as the top and bottom electrode, respectively. The n$^+$ ZnO electrode is unique, as it preserves the crystalline relationship required for multi-mode coupling with the substrate while providing an electrode function. On r-Al$_2$O$_3$, the Mg$_x$Zn$_{1-x}$O film's primary axis of symmetry lies in the surface plane. This relationship promotes shear bulk wave propagation that affords sensing in liquid phase media without the dampening effects found in longitudinal wave mode BAW devices. When a signal is applied between the top and the bottom electrodes, an acoustic shear wave mode is excited. By varying the Mg composition in the Mg$_x$Zn$_{1-x}$O films, or using ZnO/Mg$_x$Zn$_{1-x}$O heterostructure with different thickness ratio, the frequency response can be tailored, which provides an alternative and complementary method for frequency tune in addition to thickness variation.

Figure 10:
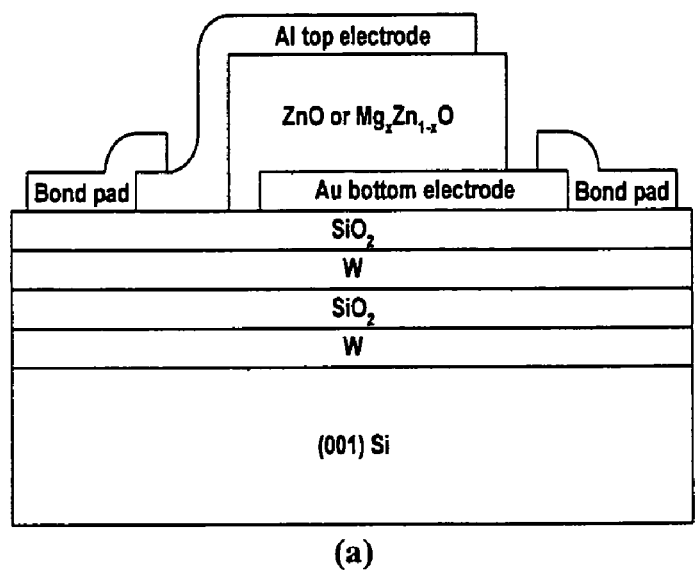
FIG. 10 (a) shows a schematic diagram of TFBAR device structure consisting of $Al/Mg_xZn_{1-x}O/Au$/acoustic mirror/Si.
Figure 10:
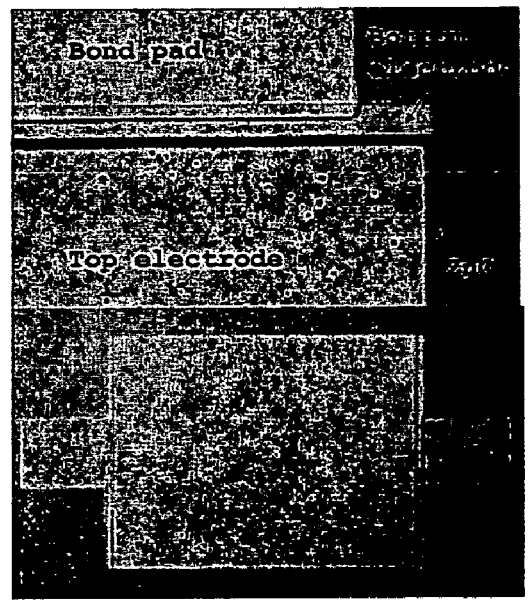

Recently, we demonstrated a single mode TFBAR using piezoelectric ZnO or Mg$_x$Zn$_{1-x}$O layers on Si substrates [15]. A complete TFR device structure consisting of Al/Mg$_x$Zn$_{1-x}$O/Au/acoustic mirror/Si is shown in FIG. 10. Al and Au layers serve as the top and bottom electrode, respectively. The acoustic mirror, composed of two periods of alternating quarter-wavelength Bragg reflector, was used to isolate the resonator from the substrate. RF sputtered Mg$_x$Zn$_{1-x}$O thin films had a preferred c-axis orientation. Thus, when a signal was applied between the top and the bottom electrodes, a longitudinal acoustic wave mode was excited.

We have also deposited ZnO nanotips on the top electrodes of TFBAR to increase the effective sensing surface area, improve the bonding strength; therefore enhance the TFBAR performance. Such ZnO nanostructured TFBAR sensors possess all the advantages of TFBAR device and ZnO nanotips.

FIG. 10 shows; (a) A schematic diagram of a ZnO or $Mg_xZn_{1-x}O/Si$ TFBAR structure, (b) optical microscope pictures and edge details of the TFBAR. The ZnO nanotips have been grown on the top of electrodes to form ZnO nanotip-based TFBAR (FIG. 7(a)).

Figure 11:
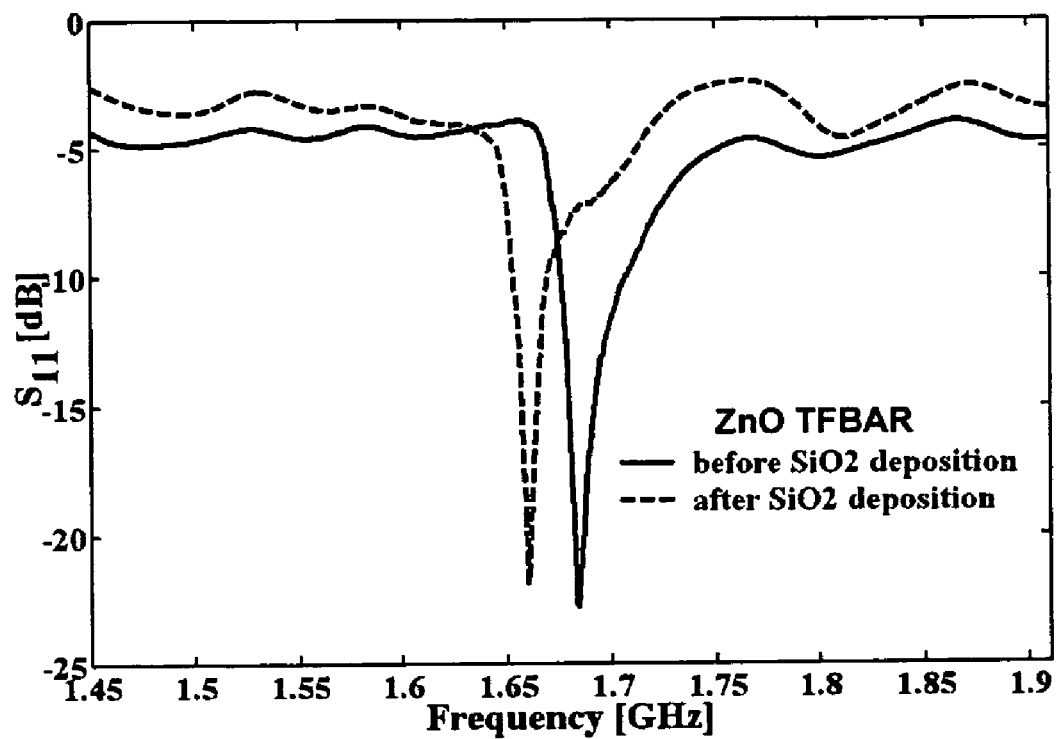
FIG. 11 shows the Measured $S_{11}$ spectra of a 150 μm×150 μm ZnO TFBAR on mirror/Si substrate, before and after $SiO_2$ deposition.

FIG. 11 shows the resonance characteristics of a 150 μm×150 μm ZnO TFBAR on mirror/Si substrate before and after mass-loading. The piezoelectric ZnO film thickness is 1.20 μm. A 60 nm $SiO_2$ thin film was deposited on top electrode to investigate the mass-sensitivity. The density of PECVD deposited $SiO_2$ is 2.3 $g/cm^3$. $\Delta m/A$ is 13.8 $\mu g/cm^2$. The measured frequency shift is 23.7 MHz. Thus, a mass sensitivity $S_f$ of 1.7 Hz $cm^2$/pg is achieved. This sensitivity is useful for ultra-sensitive-mass loading chemical sensor, biosensor, and environmental sensor applications.

Figure 12:
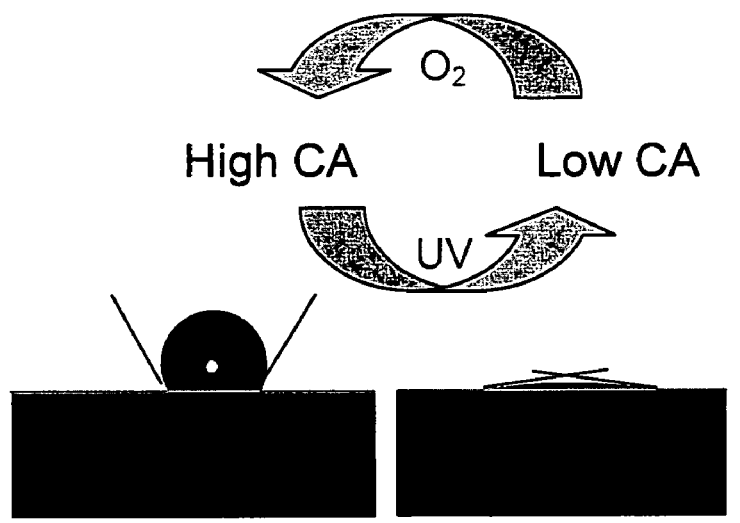
FIG. 12 shows; (a) the reversible control of wettability of ZnO nanotips, (b) the QCM responses of the ZnO nanotip-based QCMs with different wetting properties compared to the traditional QCMs.
Figure 12:
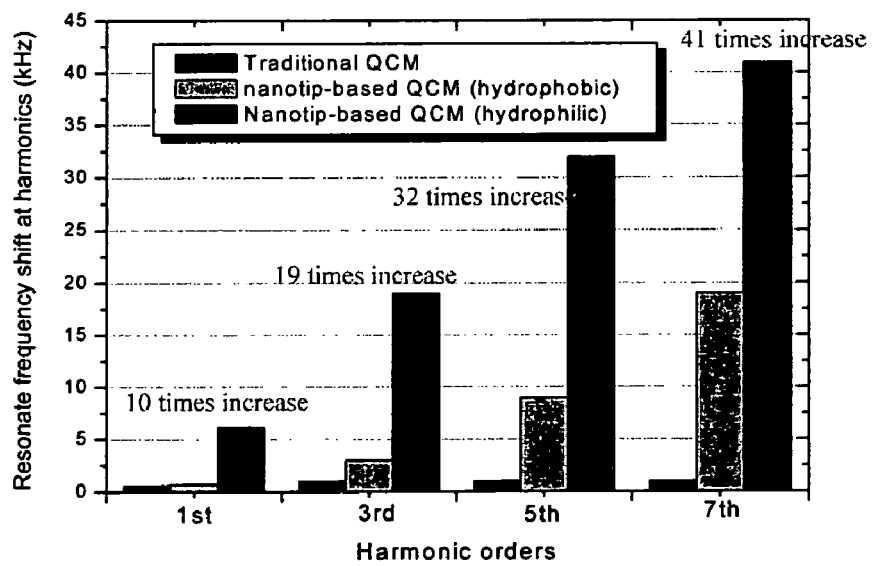

FIG. 12 shows; (a) the reversible control of wettability of ZnO nanotips, (b) the QCM responses of the ZnO nanotip-based QCM with different wetting properties compared to the traditional QCM. The wettability of ZnO nanotips can be reversibly changed between superhydrophilic status (contact angle<5 degrees) and hydrophobic status (contact angle>129 degrees). The superhydrophilic ZnO nanostructured sensor surfaces can greatly reduce the liquid consumption and further enhance the sensitivity [21, 22].

REFERENCES

The following references, to the extent that they provide exemplary procedural or other details supplementary to those set forth herein, are specifically incorporated herein by reference.

1. Y. Liu, C. R. Gorla, N. W. Emanetoglu, S. Liang, Y. Lu, "Ultraviolet detectors based on epitaxial ZnO films grown by MOCVD," J. Electronic Materials, vol. 27, p. 69, January 2000
2. P. Sharma, A. Mansingh, K. Sreenivas, "Ultraviolet photoresponse of porous ZnO thin films prepared by unbalanced magnetron sputtering," Appl. Phys. Lett., vol. 80, no. 4, p. 553, January 2002
3. H. Sheng, S. Muthukumar, N. W. Emanetoglu, Y. Lu, "Schottky diode with Ag on (11-20) epitaxial ZnO film," Appl. Phys. Lett., vol. 80, no. 12, p. 2132, Mar. 25, 2002
4. S. Liang, H. Sheng, Z. Huo, Y. Liu, Y. Lu, H. Shen, "ZnO Schottky ultraviolet photodetectors," J. Crys. Growth, vol. 225, no. 2-4, p. 110, May 2001
5. M. Wraback, H. Shen, S. Liang, C. R. Gorla, Y. Lu, "High contrast, ultrafast optically addressed ultraviolet light modulator based upon optically anisotropy in ZnO films grown on R-plane sapphire," Appl. Phys. Lett., vol. 74, no. 4, p. 507, Jan. 25, 1999
6. N. W. Emanetoglu, G. Patounakis, S. Liang, C. R. Gorla, R. H. Wittstruck, Y. Lu, "Analysis of SAW properties of epitaxial ZnO films grown on R—Al2O3 substrates," IEEE Trans. Ultrasonics, Ferroelectrics and Frequency Control, vol. 48, no. 5, p. 1389, September 2001
7. N. W. Emanetoglu, S. Muthukumar, P. Wu, R. Wittstruck, Y. Chen, Y. Lu, "$Mg_xZn_{1-x}O$: A New Piezoelectric Material," IEEE Trans. Ultrasonics, Ferroelectrics and Frequency Control, vol. 50, no. 5, p. 537, May 2003
8. R. H. Wittstruck, X. Tong, N. W. Emanetoglu, P. Wu, J. Zhu, Y. Lu, and A. Ballato, "Characterization of $Mg_xZn_{1-x}O$ Bulk Acoustic Wave Devices," IEEE Trans. Ultrasonics, Ferroelectrics and Frequency Control, vol. 50, no. 10, p. 1272, October 2003
9. N. W. Emanetoglu, G. Patounakis, S. Muthukumar, Y. Lu, "Analysis of temperature compensated SAW modes in ZnO/SiO2/Si multilayer structures," Proc. IEEE 2000 International Ultrasonics Symposium., vol. 1, no. p. 325, 2000
10. H. Sheng, N. W. Emanetoglu, S. Muthukumar, B. Yakshinskiy, S. Feng, Y. Lu, "Ta/Au Ohmic Contacts to n-type ZnO," J. Electronic Materials, vol. 32, no. 9, p. 935, September 2003
11. H. Sheng, N. W. Emanetoglu, S. Muthukumar, Y. Lu, "Non-alloyed Ohmic Contacts to $Mg_xZn_{1-x}O$," J. Electronic Materials, vol. 31, no. 7, p. 811, July 2002.
12. N. W. Emanetoglu, J. Zhu, Y. Chen, J. Zhong, Y. Chen, Y. Lu, "Surface acoustic wave ultraviolet photodetectors using epitaxial ZnO multilayers grown on r-plane sapphire", Appl. Phys. Lett. 85, p. 3702, 2004.
13. Z. Zhang, N. W. Emanetoglu, G. Saraf, Y. Chen, P. Wu, J. Zhong and Y. Lu, J. Chen, O. Mirochnitchenko, M. Inouye, "DNA Immobilization and SAW Response in ZnO Nanotips Grown on LiNbO3 Substrates", accepted by IEEE Trans. on Ultrasonics, ferroelectrics and frequency control, January 2005.
14. H. Chen, J. Zhong, G. Saraf, Y. Lu, D. H. Hill, S. T. Hsu, and Y. Ono, "Interface Properties of ZnO Nanotips Grown on Si Substrates", II-VI 2005 Workshop, will be appear Journal of Electrical Material.
15. Ying Chen, Gaurav Saraf, Richard H. Wittstruck, Nuri W. Emanetoglu, Yicheng Lu, "Studies on $Mg_xZn_{1-x}O$ Thin Film Resonator for Mass Sensor Application", 2005 Joint IEEE International Frequency Control Symposium and Precise Time and Time Interval Systems and Applications Meeting, Aug. 29-31, 2005, Vancouver, Canada
16. R. Gabl, E. Green, M. Schreiter, H. D. Feucht, H. Zeininger, R. Primig, D. Piker, G. Eckstein and W. Wersing, W. Reichl and J. Runck, "Novel Integrated FBAR Sensors: a Universal Technology Platform for Bio- and Gas-Detection", Proc. 2003 IEEE Sensors, vol. 2 pp. 1184, 2003
17. R. Gabl, H.-D. Feucht, H. Zeininger, G. Eckstein, M. Schreiter, R. Primig, D. Pitzer, W. Wersing, "First results on label-free detection of DNA and protein molecules using a novel integrated sensor technology based on gravimetric detection principles", Biosensors and Bioelectronics, 19, pp. 615, 2004
18. W. Reichl, J. Runck, M. Schreiter, E. Green and R. Gabl, "Novel gas sensor based on thin film bulk acoustic resonator", Proc. 2004 IEEE Sensors, vol. 3, pp. 1504, 2004
19. Hao Zhang, Mong S. Marma, Eun Sok Kim, Charles E. McKenna, and Mark E. Thompson, "Implantable resonant mass sensor for liquid biochemical sensing", 17th IEEE International Conference on Micro Electro Mechanical Systems, pp. 347, 2004
20. Linh Mai, Dong-Hyun Kim, Munhyuk Yim, and Giwan Yoon, "A feasibility study of ZnO-based FBAR devices for an ultra-mass sensitive sensor application", Microwave and Optical Technology Letters, vol. 42, no. 6, pp. 505, 2004
20. Zhou X C, Huang L Q, Li S F. Microgravimetric DNA sensor based on quartz crystal microbalance: comparison of oligonucleotide immobilization methods and the application in genetic diagnosis. Biosens Bioelectron. 2001 January; 16(1-2):85-95.
21. Zheng Zhang, Hanhong Chen, Jian Zhong, Ying Chen, Yicheng Lu, "ZnO Nanotip-based QCM Biosensors", *Proceeding of IEEE UFFC Frequency Control*, Miami, Fla., June 2006

22. Z. Zhang, H. Chen, J. Zhong, Y. Lu, "The Fast and Reversible Wettability Transitions of ZnO Nanostructures", the 2006 II-VI Workshop at Newport Beach, Calif. on October 10-12, will be appear Journal of Electrical Material.

While the invention has been described in relation to the preferred embodiments with several examples, it will be understood by those skilled in the art that various changes may be made without deviating from the fundamental nature and scope of the invention as defined in the appended claims.

What is claimed is:

1. A ZnO nanotip BAW resonator sensor device, comprising:
   a piezoelectric layer;
   a conductive film serving as bottom electrode deposited and patterned beneath said piezoelectric layer;
   a metal electrode serving as top electrode deposited and patterned on said piezoelectric layer;
   ZnO nanotips deposited and patterned on a top surface of said top electrode; wherein wettability (from superhydrophobicity to superhydrophilicity, or vise versa) of said ZnO nanotips can be controlled.

2. The device of claim 1 wherein said piezoelectric layer is quartz.

3. The device of claim 1 wherein said piezoelectric layer is a piezoelectric thin film, selected from a group comprising ZnO, Mg.sub.xZn.sub.1-xO, etc.

4. A thin film bulk acoustic wave resonator (TFBAR) sensor wherein the device of claim 3 is mounted on a substrate structure, including, but not limited to, an air-gap structure on the top surface of said substrate, a membrane structure on said substrate, and an acoustic mirror on top surface of said substrate.

5. The superhydrophilic status of the ZnO nanotips of claim 1 can be obtained through UV shinning.

6. The superhydrophilicity of the ZnO nanotip surface of claim 5 is used for the biosensors; wherein said superhydrophilicity reduces the liquid sample consumption and enhances the sensitivity greatly.

7. The device of claim 1 is quartz crystal microbalance (QCM).

8. The device of claim 1 is thin film bulk acoustic wave resonator TFBAR.

* * * * *